US006475717B1

(12) United States Patent
Enssle et al.

(10) Patent No.: US 6,475,717 B1
(45) Date of Patent: *Nov. 5, 2002

(54) METHOD FOR DETECTING AND DETERMINING MEDIATORS

(75) Inventors: Karlheinz Enssle, Marburg-Michelback (DE); Roland Kurrle, Niederweimar (DE); Klaus-Dieter Langner, Marburg (DE); Leander Lauffer, Gladenbach (DE); Josef-Urban Pauly, Ebsdorfergrund (DE); Friedrich-Robert Seiler, Marburg (DE)

(73) Assignee: Dade Behring Marburg GmbH, Marburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/900,576

(22) Filed: Jul. 25, 1997

Related U.S. Application Data

(63) Continuation of application No. 08/560,093, filed on Nov. 17, 1995, now abandoned, which is a continuation of application No. 08/269,619, filed on Jul. 1, 1994, now abandoned, which is a continuation of application No. 08/111,908, filed on Aug. 26, 1993, now abandoned.

(30) Foreign Application Priority Data

Aug. 29, 1992 (DE) .......................................... 42 28 839

(51) Int. Cl.$^7$ .......................... C12Q 1/70; G01N 33/53; G01N 33/543
(52) U.S. Cl. ............................... 435/5; 435/6; 435/7.8; 435/7.94; 436/501; 436/518
(58) Field of Search ..................... 435/5, 6, 7.8, 7.94; 436/501, 518

(56) References Cited

U.S. PATENT DOCUMENTS

| 5,198,340 A | | 3/1993 | Mukku |
| 5,639,597 A | * | 6/1997 | Lauffer et al. ................. 435/5 |

FOREIGN PATENT DOCUMENTS

| DE | 4 020 607.6 | 6/1990 |
| EP | 0 257 541 | 3/1988 |
| EP | 0 314 317 A1 | 5/1989 |
| EP | 0 325 262 A2 | 7/1989 |
| EP | 0 330 050 | 8/1989 |
| EP | 0 330 977 | 9/1989 |
| EP | 0 464 533 A1 | 1/1992 |
| EP | 0 488 170 A1 | 6/1992 |

OTHER PUBLICATIONS

Sergio Romagnani, "Human $T_H1$ and $T_H2$ Subsets: Doubt No More," Immunology Today, 12(8):256–257 (1991).
K.J. Else et al., "Helper T–cell Subsets in Mouse Trichuriasis," Parasitology Today, 7(11):313–316 (1991).
John J. Siekierka et al., "Radioiodination of Interleukin 2 to High Specific Activities by the Vapor–Phase chloramine T method," Analytical Biochemistry, 172:514–517 (1988).
Ivan C. King et al., "Nonradioactive Ligand Binding Assay for Epidermal Growth Factor Receptor," Analytical Biochemistry, 188:97–100 (1990).
Rejean L. Idzerda et al., "Human Interleukin 4 Receptor Confers Biological Responsiveness and Defines A Novel Receptor Superfamily," J. Exp. Med., 171:861–873 (1990).
Charles R. Maliszewski et al., "Cytokine Receptors and B Cell Functions," The Journal of Immunology, 11:3028–3033 (1990).
Gerd Zettlmeissl et al., "Expression and Characterization of Human CD4: Immunoglobulin Fusion Proteins," DNA and Cell Biology, 9(5):347–353 (1990).
John C. Winkelmann et al., "The Gene for the Human Erythropoietin Receptor: Analysis of the Coding Sequence and Assignment to Chromosome 19p," Blood, 76(1):24–30 (1990).
Hideaki Tanimori et al., "A Sandwich Enzyme Immunoassay of Rabbit Immunoglobulin G with an Enzyme Labeling Method and a New Solid Support," Journal of Immunological Methods, 62:123–131 (1983).
Te Piao King et al., "Preparation of Protein Conjugates via Intermolecular Disulfide Bond Formation," Biochem., 17(8):1499–1506 (1978).
Watson et al., "A Homing Receptor—TgG Chimera as a Probe for Adhesive Ligands of Lymph Node High Endothelial Venules," J. Cell Biol., 110:2221–2229, (1990).
Niendorf, et al., "Visualization of Binding Sites for Bovine Parathyroid Hormone (PTH 1–84) on Cultured Kidney Cells with a Biotinyl–b–PTH (1–84) Antagonist," J. of Histochemistry and Cytochemistry, 34 (3), 357–361 (1986).
Smith, et al., "A Receptor for Tumor Necrosis Factor Defines an Unusual Family of Cellular and Viral Proteins," Science, 248, 1019–1023 (1990).
Gearing, et al., "Expression Cloning of a Receptor for Human Granulocyte–Macrophage Colony–Stimulating Factor," EMBO J., 8 (12), 3667–3676 (1989).
Aruffo, et al., "Molecular Cloning of a CD28 cDNA by a High Efficiency COS Cell Expression System," Proc. Natl. Acad. Sci., 84, 8573–8577 (1987).
Seed, "An LFA–3 cDNA encodes a Phospholipid–linked Membrance Protein Homologous to Its Receptor CD2," Nature 329, 840–842, (1987).
Simmons, et al. "The Fcγ Receptor of Natural Killer Cells is a Phospholipid–Linked Membrane Protein," Nature 333, 568–570 (1988).

* cited by examiner

Primary Examiner—Donna C. Wortman
(74) Attorney, Agent, or Firm—Finnegan, Henderson, Farabow, Garrett and Dunner, L.L.P.

(57) ABSTRACT

The invention relates to a method for detecting and determining mediators and/or their derivatives in fluids, the mediator being detected directly or indirectly with the aid of a recombinant, soluble receptor for the mediator to be detected.

21 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

AGGCAGCTGC TGACCAAGCT TTGGACTGTG CCGGGGGC    38

(2) INFORMATION FOR SEQ ID NO:2:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

AGAGCCTCAG GATGAGGGGA TCCAGGTCGC TAGCGC    36

METHOD FOR DETECTING AND DETERMINING MEDIATORS

This application is a continuation, of application Ser. No. 08/560,093 filed Nov. 17, 1995, now abandoned, which is a continuation of application Ser. No. 08/269,619, filed Jul. 1, 1994, abandoned which is a continuation of application Ser. No. 08/111,908, filed Aug. 26, 1993, now abandoned.

The invention relates to a method for detecting and determining mediators and/or their derivatives.

Mediators are, e.g., interleukins, such as IL-1, TNF, IL-8 or IL-4, cytokinos, such as GM-CSF, G-CSF or Meg-CSF, or alternatively erythropoietin. Mediators are important signal proteins which are secreted by particular cells of the body, such as lymphocytes, and can act in a regulatory manner on these same cells or on other cells of the body. Such mediators can exert this regulatory function at very low concentration. In pathological states of disease, the natural cooperation of different mediators can be disturbed. Under these circumstances, mediators can, compared to average concentrations of these mediators in average healthy persons, be present at higher or lower concentration. From the diagnostic point of view, it is important to determine the concentration of particular mediators in body fluids or other sources, such as organ homogenates. Moreover, patients can be treated with particular mediators for therapeutic or prophylactic purposes. Here, too, it is of great interest from the diagnostic point of view to determine the concentration of the mediator which has been administered, or of other mediators whose concentrations are altered through the influence of the administered mediator. Thus, for example, the appearance of IL-4 in the persons with allergic diseases or infections can be altered in a pathological manner as compared with healthy persons. The reason for this can be the increased appearance, often occurring in such diseases, of T-lymphocytes of the TH2 subpopulation, which, as compared with the TH1 subpopulation, preferentially produces inter-leukin-4 (S. Romagnani, Immunology Today, Vol. 12, No. 8, 256–257, 1991; Else and Grencis, Parasitology Today, Vol. 7, No. 11, 313–316, 1991). In addition, it is important from the diagnostic point of view to determine mediators in supernatants of cell cultures of lymphocytes or other cells.

Mediators, such as those listed above, exert their positive or negative effect via receptors located in the membrane. These receptors bind, via a defined binding site, to a defined epitope of a mediator. Subsequently, a signal transduction takes place via the receptor and/or associated molecules into the cell in which a biological effect takes place as a result. The biological effect of such a mediator is consequently strictly linked to optimal binding to the binding site on the receptor located in the membrane. For example, substances or mediators which do not bind directly to the binding site, but instead to other epitopes on the receptor, may not trigger any signal transduction.

It has now been found, surprisingly, that recombinant, soluble receptors for these mediators can be used for detecting the presence and the concentration of mediators in liquids.

The invention therefore relates to a method for detecting and determining mediators and/or their derivatives in liquids where a recombinant, soluble receptor for the mediator to be detected is brought into contact with a sample, which can contain the mediator, and the mediator bound to the receptor is detected directly or indirectly by an antibody which is specific for the mediator.

In an advantageous method, dimers or multimers of the mediator, or derivatives thereof, are determined.

In a further advantageous method, the receptor, or derivatives thereof, is bound to a solid phase.

In another advantageous method, a recombinant fusion protein comprising a receptor and the Fc moiety of antibodies, or derivatives thereof, is bound to the solid phase via Fc-specific antibodies.

In a particularly advantageous method, the receptor, or derivatives thereof, is bound to the solid phase via specific antibodies, and, subsequently, sample material containing the corresponding mediator to be determined is applied, and the mediator is detected using a labeled antibody or antiserum having specificity for the mediator.

In a very particularly advantageous method, a recombinant fusion protein comprising a receptor and the Fc moiety of antibodies, or derivatives thereof, is bound to the solid phase via Fc-specific antibodies and, subsequently, sample material containing the corresponding mediator to be determined, or derivatives thereof, is applied, and the bound mediator is detected using a labeled antibody or antiserum having specificity for the mediator.

In another advantageous method, conjugates comprising a receptor, or derivatives thereof, coupled to substances which are suitable for the detection in suitable measuring systems are used to detect a mediator, and/or derivatives thereof, which is bound to a solid phase, for example via specific antibodies.

The invention furthermore relates to the use of such a method for screening for agonists or antagonists of the mediator or of the receptor.

The invention also relates to the use of such a method for determining the affinity between a mediator and its receptor.

The invention likewise relates to the use of such a method for identifying and analyzing modified mediators ("muteins") or parts of the mediators (for example oligopeptides).

In this context, it is advantageous to use the method for identifying and analyzing substances which influence the interaction of pathogenic organisms (for example viruses or bacteria) with their cellular receptors. It is particularly advantageous to use such a method for identifying substances which influence the interaction of cellular adhesion molecules.

In a particularly advantageous method, the receptor is a cytokine receptor, a growth hormone receptor, a hormone receptor, a neurotransmitter receptor, or a cellular receptor for a pathogenic organism, e.g. a virus.

In a very particularly advantageous method, the receptor is the interleukin-4 receptor or a derivative thereof, an erythropoietin receptor, or a derivative thereof, the interleukin 1 receptor type I or type II or a derivative thereof, the interleukin 7 receptor or a derivative thereof, the GM-CSF receptor or a derivative thereof or the IL-8 receptor or a TNF receptor or a derivative thereof.

The invention also relates to a method of this type for the diagnostic detection of interleukin-4 in diseases exhibiting an increased appearance of TH2 T-cells, for example allergic diseases and infections.

The use of the natural, biologically important, receptor binding site for detecting the corresponding mediator is particularly advantageous since only those mediator molecules are determined which would also bind to the natural receptor, located in the membrane, and consequently are biologically active.

For the purposes of this invention, receptors are also understood to mean all variants and derivatives which are capable of binding the corresponding mediator specifically.

The detection can be carried out by binding the recombinant soluble receptor, under suitable conditions, to the solid phase of the detection system, for example the synthetic material of a microtitration plate. Such solid phases are known per se to the person skilled in the art. Advantageous solid phases are: magnetic particles, particles composed of natural or synthetic polymers, e.g. so-called latex particles or ion-exchange resins or synthetic polymers in the form of covalent or convex articles, such as, e.g., microtitration plates or spheres. Magnetizable particles, latex particles or microtitration plates are particularly advantageous. Microtitration plates are very particularly advantageous. Although the receptor is not present in the form in which it is located within the membrane, it surprisingly binds the corresponding epitope on the corresponding mediator with the affinity of the natural, membrane-bound receptor. The bound mediator can then be detected by methods which are known per se to the person skilled in the art. For this, the bound mediator can be coupled with one or more monoclonal antibodies, which are directed against a further epitope on the mediator, or an antiserum, which is directed against several further epitopes on the mediator.

In order to detect a bound antiserum or a bound, monoclonal antibody, the latter can be coupled directly to corresponding substances or proteins. Such signal-yielding components are known as such to the person skilled in the art; they are substances or proteins which permit quantitative detection, e.g. using radioactive nuclides, or which make possible an enzymically catalyzed color reaction, e.g. using coupled peroxidase, or permit the enzymatically catalyzed production of substances which allow detection by means of luminescence or fluorescence. It is advantageous to use a luminescence label, and in this context particularly advantageous to use the compounds described in EP 0,257,541 and EP 0,330,050.

The antiserum or the monoclonal antibody can also be coupled to magnetizable particles.

For the detection using a radioactive nuclide, the method of Siekierka, J. J. and De Gudicibus, S., Anal. Biochem. Vol. 172 (1988), 514–517 can be used, for example. For detection by means of a color reaction, the antiserum or one or more monoclonal antibodies can also be biotinylated (King and Catino, Anal. Biochem. Vol. 188 (1990), 97–100). The biotin can in turn be detected either by avidin or by anti-blotin, to which substances or proteins are coupled which permit the above-listed detection methods. For example, this can be a conjugate between avidin and peroxidase.

The detection of mediators using corresponding recombinant soluble receptors can also be effected by using variants of the receptor which are bound indirectly to the solid phase, e.g. a microtitration plate, via specifically binding proteins. A variant such as this can be a recombinant fusion protein between the extracellular domain of the receptor, or parts thereof, and the Fc moiety, or parts thereof, of immunoglobulins, for example IgG-Fc of the same species or of other species. In this case, one or more monoclonal antibodies, or an antiserum, which react specifically with the Fc moiety of the fusion protein, can first be bound to the solid phase, e.g. a microtitration plate. This monoclonal antibody or this antiserum then binds the receptor fusion protein specifically. This has the advantage that the conformation of the receptor is preserved more effectively.

If, in addition, an Fc moiety or moieties from another species is used for the recombinant fusion with the receptor instead of the homologous Fc moiety, cross reactions in the detection of a mediator from physiological body fluids, which may also contain Fc-bearing proteins, are excluded.

The detection of mediators using corresponding recombinant soluble receptors can also be effected by first binding to the solid phase, e.g. to a microtitration plate, one or more monoclonal antibodies, or an antiserum, which react with other, or several other, epitopes on the mediator than the corresponding receptor. Subsequently, the mediator is bound to the specific antibodies of the solid phase. The corresponding receptor is then bound to the bound mediator. Substances or proteins can be coupled to the receptor which, as explained above, permit quantitative detection.

If, as set out above, Fc-fusion proteins of the receptor are used, the receptor proteins can then be detected by suitable Fc-specific substances or proteins which either permit direct quantitative determination or are in turn coupled to substances or proteins which permit such a quantitative measurement. For example, the Fc moiety or moieties of the recombinant fusion protein can be detected by means of biotinylated monoclonal antibodies or antisera which themselves can be detected by means of an avidin-peroxidase conjugate. Such a Fc-specific detection could, for example, take place using a biotinylated monoclonal antibody against the CH2 domain of the Fc moiety. If, in addition, an Fc moiety, or parts thereof, from another species is used for the recombinant fusion with the receptor instead of the homologous Fc moiety, cross reactions in the detection of a mediator from physiological body fluids, which also contain Fc-bearing proteins, are also excluded.

Recombinant receptors are also used for detecting biologically active dimers or multimers of the corresponding mediator. For example, tumor necrosis factor alpha is present as a trimer under physiological conditions. Dimers or trimers of mediators can also be prepared synthetically or by recombinant means. The detection of such dimers or oligomers is carried out by using recombinant receptors in an assay of the sandwich type both for binding the dimer or oligomer to the solid phase and for detecting dimer or oligomer bound thereon via the epitopes which remain available. The detection can also be carried out by using receptors, or variants thereof, which are labeled with different detection substances.

The detection of dimers or oligomers can also be effected by binding one epitope, in the case of dimers, or one or more epitopes, in the case of oligomers, by means of a receptor, which is correspondingly labeled or bound to the solid phase, and detecting the epitopes which remain available by means of monoclonal antibodies which neutralize the biological effect of the corresponding mediator and are labeled in a suitable way for the detection. For example, MTP (microtitration plates) can be layered with 100 µl per well of a monoclonal or polyclonal anti-human IgG antibody in PBS having a concentration of 5 µg/ml. After an incubation period of 24 h at room temperature, the MTP can be washed several times with a buffer solution, dried and packed individually in an air-tight manner together with a drying agent. These ready-to-use MTP can be stored over a relatively long period of time.

For detecting EPO dimer, these plates are washed twice, before the beginning of the test, with a washing solution (WB, comprising PBS containing 0.05% Tween 20). 100 µl of an EPO-R-Fc solution (100 ng/ml in WB) are then dispensed into all the wells and the plates are incubated at 37° C. for 30 min. Any remaining free Fc-binding sites are then blocked off with 10% human serum (Behringwerke Marburg, FRG). After washing several times, 100 µl of a serial dilution series of the bioactive EPO dimer (recombinant human EPO-Fc fusion protein) are in each case subsequently pipetted into a well. The binding of the EPO dimer in the samples then takes place at room temperature during 2 h. After washing several times with WB, the bound EPO-Fc is detected by means of the addition of an EPO-receptor-enzyme conjugate. For this purpose, 100 µl of an EPO-receptor-horseradish peroxidase conjugate (0.5 µg/ml in WB+2% bovine albumin) are dispensed into each well. After an incubation of 1 h at room temperature, the MTP are washed several times. A signal is subsequently generated by the oxidation of o-phenylenediamine using the immobilized peroxidase.

The above-listed possibilities for detecting mediators with the aid of recombinant receptors, or variants thereof, can be used in many ways.

Natural or recombinant mediators can be detected. The mediators can be detected in purified form, diluted in a suitable test liquid, or out of natural body fluids, such as blood plasma, blood sera, whole blood, urine, stool samples, ocular fluid, gastric fluid, cerebrospinal fluid or sputum, or in suitably prepared organ homogenates, or in supernatants of cell cultures of body cells in a suitably prepared form.

The detection methods can additionally be used:
to instigate a receptor screening, i.e. in order to find agonists or antagonists which inhibit or promote the interaction between a mediator and its corresponding receptor;
in order to determine the binding activity of a receptor or a ligand;
for identifying and analyzing modified mediators ("muteins") or parts of the mediators (e.g. oligopeptides);
for identifying and analyzing substances which influence the interaction of pathogenic organisms (e.g.; viruses or bacteria) with their cellular receptors;
for identifying substances which influence the interaction of cellular adhesion molecules.

The following examples serve to illustrate the invention but do not limit it.

Abbreviations employed:

| | |
|---|---|
| BHK | Baby hamster kidney cells |
| BSA | Bovine serum albumin |
| EPO | Erythropoietin |
| EPOR-Fc | Erythropoietin receptor fusion protein with human IgG1-Fc (recombinant, soluble) |
| G-CSF | Granulocyte colony stimulating factor |
| GM-CSF | Granulocyte macrophage colony stimulating factor |
| IL-1 | Interleukin-1 |
| IL-2 | Interleukin-2 |
| IL-4 | Interleukin-4 |
| IL-4R | Interleukin-4 receptor (recombinant, soluble) |
| IL-4R/Fc | Interleukin-4 receptor fusion protein with the Fc-moiety of an immunoglobulin (recombinant, soluble) |
| IL-6 | Interleukin-6 |
| IL-7 | Interleukin-7 |
| Meg-CSF | Megakaryocyte colony stimulating factor |
| MTP | Microtitration plates |
| PBS | Phosphate-buffered saline |
| PCR | Polymerase chain reaction |
| POD | Peroxidase |
| Th1 | Type 1 T-helper lymphocytes |
| TH2 | Type 2 T-helper lymphocytes |
| TMB | Tetramethylbenzidine |
| TNF | Tumor necrosis factor |
| WRA | Washing solution A |
| WBB | Washing solution B |

IL-4R can, for example, be prepared according to the international Patent Application WO 90/05183.

EXAMPLE 1

Immunoreceptor assay method for determining the presence and the concentration of human IL-4 in liquid samples For examples 1 and 2, the extracellular regions defined in Idzerda et al. (1990, J. Exp. Med. 171, 861–873) and Maliszewski et al. (1990, J. Immunol. 144, 30283033), or naturally occurring soluble forms, of human or murine IL-4 receptor (designated below as huIL-4R and muIL-4R, respectively) were used, which were secreted as soluble protein into the culture medium by stably expressing BHK cells after double selection with methotrexate and G418 (EP-A 0,330,977) and which were purified by means of immunoaffinity chromatography. In addition, receptor/ immunoglobulin fusion proteins (EP-A1-0,464,533) were used which comprise the extracellular region of human or murine IL-4 receptor having the hinge, CH2 and CH3 domains of a human IgG1 molecule or of a murine IgG2b molecule (Zettlmeiβ1 et al. (1190) DNA and Cell Biol. 9, 347–353) (designated below as huIL-4R/Fc and muIL-4R/ Fc, respectively) and which likewise were purified by means of protein A-Sepharose affinity chromatography following expression in BHK cells.

MTP were coated at 4° C. for 16 h, at a volume of 100 µl per test well, with PBS containing 5 µg/ml of recombinant, human IL-4R or IL-4R/Fc. Subsequently, the plates were washed three times with PBS containing 0.05% (w/v) Tween-20 and 0.1% (w/v) BSA (designated below as washing buffer (WBA)) in order to remove unbound coating material. Subsequently, the plates were. incubated at 37° C., with a 200 µl volume of buffer per test well, for 2 h with PBS containing 0.05% (w/v) Tween-20 and 2% (w/v) BSA in order to block free binding sites. Human recombinant IL-4 (Immunex, Seattle, USA, Lot 1898-022) was then diluted in WBA to the given test concentrations, and applied. The test plates were then incubated at 37° C. for 90 min. Subsequently, the test plates were washed three times with WBA as described above in order to remove unbound IL-4. To detect bound IL-4, a rabbit antiserum having specificity for human IL-4 (BL4P) (Genzyme, Cambridge, USA) was then diluted to a concentration of 2 µg/ml in WBA and added at a volume of 100 µl per test well. Incubation then took place at 37° C. for 90 min. Subsequently, unbound antiserum was removed by washing three times with WBA. To detect the bound antiserum, biotinylated goat antiserum having specificity for rabbit immunoglobulin (A0207, Vector Inc., Burlingame, USA) was diluted to a concentration of 0.15 µg/ml in WBA and added at a volume of 100 µl per culture well, and the plates were incubated at 37° C. for 1 h. In order to remove unbound antiserum, the plates were then washed three times with WBA. Subsequently, streptavidin-POD (RPN 1213,44B, Amersham, UK), diluted to a test dilution of 1:2000 in WBA, was added at a volume of 100 µl per test well, and the plates were incubated at 37° C. for 1 h. For the enzymatic detection of the bound streptavidin-POD conjugate, and thus indirectly. of the bound IL-4, the chromogen TMB (OUVF 925, Behringwerke, Marburg, FRG) was diluted 1:10 with Behring substrate buffer (Behringwerke Marburg, FRG, OUVG 945) and added to the test plates at a volume of 100 µl per culture well. Incubation then took place at room temperature for 1 h. Subsequently, the reaction was stopped with 0.5 N sulfuric acid at a volume of 100 µl per culture well and the extinction of the individual culture wells was measured at 450 nm, reference wave length 650 nm.

In each case the average values of duplicate determinations are given with the coefficient of variation (C.V. in %). The results are presented in Table 1A. At the same coating concentration, a somewhat higher background and a higher extinction overall was observed with huIL-4R/Fc as compared with huIL-4R. However, this has no effect on the detection sensitivity for human IL-4. The reaction was highly specific. No reaction took place if murine IL-4 was employed instead of human IL-4. Additionally, other mediators, e.g. human IL-1-α, IL-1-β, human TNF-α, human TNF-β, human IL-2, human IL-6 and human IL-7, showed no reaction. These controls were carried out using IL-4R/Fc as the coating material and are presented in Table 1B. In each case, the average values of duplicate determinations are given with the coefficient of variation (C.V. in %). In the controls, the extinctions were converted into concentrations (pg/ml) using the standard curve, but were in each case below background. The detection can also be carried out when human IL-4 is present, for example, in culture medium or serum.

EXAMPLE 2

Immunoreceptor assay method for determining the presence and the concentration of murine IL-4 in liquid samples Murine IL-4R/Fc was prepared as described in Example 1. MTP were coated at 4° C. for 16 h, and at a volume of 100 µl per test well, with PBS containing 5 µg/ml of recombinant murine IL-4R/Fc. Subsequently, the plates were washed three times with PBS containing 0.05% (w/v) Tween-20 and 0.1% (w/v) BSA (designated below as WBA) in order to remove unbound coating material. The plates were then incubated at 37° C., and at a buffer volume of 200 µl per test well, for 2 h with PBS containing 0.05% (w/v) Tween-20 and 2% (w/v) BSA in order to block free binding sites. Murine recombinant IL-4 (Lot 2871-023, Immunex, Seattle, USA) was then diluted in WBA to the given test concentrations and applied. The test plates were then incubated at 37° C. for 90 min. Subsequently, the test plates were washed three times with WBA as described above in order to remove unbound IL-4. For the detection of bound IL-4, a rat monoclonal antibody having specificity for murine IL-4 (MM450 D Lot 103023, Endogen, Boston, USA) was diluted to a concentration of 2 µg/ml in WBA and added at a volume of 100 µl per test well. Incubation then took place at 37° C. for 90 min. After that, unbound monoclonal antibody was removed by washing three times with WBA. To detect the bound antibody, biotinylated goat antiserum having specificity for rat immiunoglobulin (3010-08 Lot-B022 N222, Southern Biotechnology Assoc., Birmingham, USA) was diluted to a concentration of 0.25 µg/ml in WBA and added at a volume of 100 µl per culture well, and the plates were then incubated at 37° C. for 1 h. The plates were then washed three times with WBA in order to remove unbound antiserum. Subsequently, streptavidin-POD (RPN 1213,44 B, Amersham, UK), diluted to a test dilution of 1:2000 in WBA, was added at a volume of 100 µl per test well and the plates were incubated at 37° C. for 1 h. For the enzymatic detection of the bound streptavidin-POD conjugate, and thus of the bound IL-4, the chromogen TMB (Behringwerke Marburg, FRG, OUVF 925) was diluted 1:10 with Behring substrate buffer (Behringwerke Marburg, FRG, OUVG 945) and added to the test plates at a volume of 100 µl per culture well. The plates were next incubated at room temperature for 1 h. Subsequently, the reaction was stopped with 0.5 N sulfuric acid, at a volume of 100 µl per culture well, and the extinction of the individual culture wells was measured at 450 nm, reference wave length 650 nm. The results are presented in Table 2A. The reaction was highly specific. No reaction took place if, instead of murine IL-4, human IL-4 or other mediators, e.g. murine IL-1-α, murine IL-1-β, or murine TNF-α, was used. These controls are presented in Table 2B. In each case, the average values of duplicate determinations are given with the coefficient of variation (C.V. in %). In the controls, the extinctions were converted into concentration (pg/ml) using the standard curve, but were in each case below background. The detection can also be carried out when murine IL-4 is present, for example, in culture medium or serum.

EXAMPLE 3

Immunoreceptor assay method for determining the presence and the concentration of bioactive EPO in liquid samples using a combination comprising solid-phase-bound anti-EPO antibody (monoclonal or polyclonal) and an EPO-receptor-enzyme conjugate cDNA encoding the human EPO receptor has recently been isolated (Winkelmann et al., (1990), Blood 76, 24–30). Two oligonucleotides were synthesized which can hybridize with sequences in the 5'-untranslated region (A: 5'AGG CAG CTG CTG ACC AAG CTT TGG ACT GTG CCG GGG GC 3') (SEQ ID NO:1) and in the coding region (B: 5' AGA GCC TCA GGA TGA GGG GAT CCA GGT CGC TAG CGC 3') (SEQ ID NO:2), respectively, of the EPO receptor cDNA. Oligonucleotide A is partially homologous to the sequence of the coding strand and contains a Hind III restriction site; oligonucleotide B is partially homologous to the non-coding strand and contains a BamH I restriction site. PCR on the EPO receptor cDNA, using the two oligonucleotides A and B, yields a DNA fragment which contains the complete coding sequence for the extracellular region of the EPO receptor. The reading frame in the BamH I restriction site introduced by oligonucleotide B is such that the nucleotide sequence GAT is translated as aspartic acid. The PCR fragment was treated with Hind III and BamH I and ligated into the pCD4E gamma 1H-Vector backbone, which had been opened with Hind III and BamH I. The resulting plasmid was given the designation pEPORFc. pCD4E gamma 1H is the vector pCD4E gamma 1, known from EP 0,325,262 A2, in which the Hind III restriction site located downstream from the unique BamH I restriction site has been deleted by partial restriction with Hind III, filling in the Hind III protruding ends with the aid of Klenow enzyme, and religating. pEPORFc encodes the protein EPORFc comprising the extracellular region of the human EPO receptor fused to hinge, CH2 and CH3 domains of a human IgG1 molecule (EP 0,464,533 A1). pEPORFc was transfected into BHK cells and stable clones were obtained following double selection with methotrexate and G418 (EP 0,330,977). Typical rates of expression were in the region of 5 µg per ml of supernatant, from which EPORFc was isolated by means of chromatography on protein A-Sepharose (EP 0,464,533 A1).

MTP were coated, at a volume of 100 µl per well, with isotonic PBS containing a concentration of 5 µg/ml of a monoclonal or polyclonal anti-EPO antibody which recognizes an epitope which is different from, and independent of, the receptor binding site. After an incubation period of 24 h at room temperature, the MTP were washed several times with 0.05 M Tris/citrate, dried and packed individually in an air-tight manner together with a drying agent. These ready-to-use MTP can be stored over a relatively long period of time. Before beginning the assay, the plates were washed twice with a WBB (comprising PBS containing 0.05% Tween 20). Subsequently, 100 µl of a serial dilution series of recombinant human EPO are in each case pipetted into a well. The binding of the EPOs in the samples takes place at room temperature over the course of 2 h. After washing several times with WBB, the bound EPO was detected by the addition of the EPO-receptor-enzyme conjugate. For this purpose, 100 µl of an EPO-receptor-Fc-horseradish peroxidase conjugate (0.5 µg/ml in WBB+2% BSA) were dispensed into each well. After being incubated at room temperature for 1 h, the MTP were washed several times. A signal was generated by means of the oxidation of o-phenylenediamine using the POD. Subsequently, it was possible to measure the extinction at 492 nm, reference wave length 650 nm.

The EPO-receptor-Fc-horseradish peroxidase conjugate was synthesized in the following way: The receptor-Fc fusion protein was first converted into the maleimido derivative by the method of Tanimore et al., J. Immunol. Meth. 62, pp. 123–131 (1983). In parallel, horseradish peroxidase (Boehringer-Mannheim, Mannheim) was SH-activated according to King et al., Biochemistry 17, pp. 1499–1506 (1978) and added to the maleimido-EPO-receptor fusion protein, resulting in the formation of stable enzyme conjugates. Tables 3A–C illustrate the results of this "sandwich-type" immunoreceptor assay for EPO. Use was made of an EPO-receptor-Fc-fusion-protein-peroxidase conjugate for the detection, and of different monoclonal or polyclonal antibodies bound to the solid phase. As the results show, this type of test system is able to detect the presence and the concentration of bioactive EPO down to 2 µg/ml or less.

EXAMPLE 4

Immunoreceptor assay method for determining the presence and the concentration of bioactive EPO in liquid samples using a combination comprising solid-phase-bound anti-human IgG antibody, an EPO-R-Fc fusion protein and different EPO-antibody-enzyme conjugates which recognize an epitope which is different from that of the receptor binding site MTP were coated, at 100 µl per well, with PBS containing concentration of 5 µg per ml of a monoclonal or polyclonal anti-human IgG antibody. After an incubation period of 24 h at room temperature, the MTP were washed several times with 0.05 M Tris/citrate, dried and packed individually in an air-tight manner together with a drying agent. These ready-to-use MTP can be stored over a relatively long period of time. Before beginning the assay, the plates were washed twice with a WBB, (comprising PBS containing 0.05% Tween 20). 100 µl of an EPO-R-Fc solution (100 ng/ml in WBB) were dispensed into all the wells, and the plates were incubated at 37° C. for 30 min. After the plates had been washed several times, 100 µl of a serial dilution series of recombinant human EPO were in each case pipetted into a well. The binding of the EPO in the samples took place at room temperature over the course of 2 h. After washing the plates several times with WBB, the bound EPO was detected by the addition of an anti-EPO-antibody-enzyme conjugate (Behringwerke, Marburg, FRG). For this, 100 µl of an anti-EPO-antibody-horseradish peroxidase conjugate (0.5 µg/ml in WB+2% BSA) were dispensed into each well. After an incubation of 1 h at room temperature, the MTP were washed several times. A signal was generated by the oxidation of o-phenylenediamine using the POD.

The anti-EPO-antibody-POD conjugate was synthesized as already described above for the EPO-receptor fusion protein.

Tables 4A–D illustrate the results of this "sandwich-type" immunoreceptor assay for EPO. Use was made of an EPO-receptor-Fc fusion protein bound to a solid-phase-fixed anti-human IgG antibody, and of different anti-EPO-antibody-peroxidase conjugates.

As the results show, this type of test system is able, as in Example 3, to detect the presence and the concentration of bioactive EPO down to 2 µg/ml or less.

EXAMPLE 5

Immunoreceptor assay for detecting the presence and the concentration of bioactive EPO dimers and oligomers in liquid samples according to Example 1 or 2 using a monoclonal antibody which can competitively inhibit the binding of the receptor to EPO The example was carried out as described under Example 4 except that, after incubation with EPO-R/Fc, any remaining free Fc binding sites were blocked by incubation with 10% human serum (Behringwerke Marburg, FRG), and the monoclonal antibodies (89-146-057) which were employed can competitively inhibit the binding of the receptor to erythropoietin. A fusion protein comprising human EPO and a human Fc-gamma (1) fragment, which is dimerised during biosynthesis in the cell (EP 0,464,533 A1), was used as the active EPO dimer. This fusion protein was purified by means of protein A affinity chromatography and is biologically active. To prepare biologically inactive dimers/oligomers, recombinant human EPO was cross-linked with glutaric dialdehyde and the EPO dimers/oligomers were separated subsequently from the remaining EPO monomer by means of gel permeation chromatography.

The corresponding data for this immunoreceptor assay for determining the presence and the concentration of biologically active EPO dimers/oligomers are summarized in Table 5. Use was made of an EPO-receptor-Fc fusion protein bound to a solid-phase-fixed anti-human IgG antibody, and of the peroxidase conjugate of the neutralizing-anti-EPO antibody 89-146-057. As the results show, this test system can distinguish between biologically active and non-active EPO dimers/oligomers and is able to detect the presence and the concentration of bioactive dimers/oligomers down to 1 µg/ml and less.

EXAMPLE 6

Detection of GM-CSF by means of a GM-CSF-receptor/Fc fusion protein

The plasmid pGM-CSFR/Fc is known from DE-A-40 20 607. It encodes the protein GM-CSFR/Fc, comprising the extracellular region of the human GM-CSF receptor fused to hinge, CH2 and CH3 domains of a human IgG1 molecule (EP 0,464,533 A1). pGM-CSFR/Fc was transfected into BHK cells and stable clones were obtained following double selection with methotrexate and G418 (EP 0,330,977). Typical expression rates were in the region of 10 µg/ml of supernatant, from which GM-CSFR/Fc was isolated by means of chromatography on protein A-Sepharose (EP 0,464,533 A1). MTP were pre-coated with a rabbit antiserum against the CH2 domain of a human IgG1 molecule (DE P 4020 607.6). GM-CSFR/Fc (100 µl, 3 µg/ml in PBS containing 10% BSA) were bound to this solid phase (room temperature, 1 h). After the plates had been washed three times with PBS containing 0.05% Tween-20 (WBB), any remaining free CH2 binding sites on the solid phase were saturated by incubation with 20% human serum in PBS containing 10% BSA (100 µl, room temperature, 1 h). After that, incubation took place with the concentrations of recombinant human GM-CSF in PBS containing 1% BSA which are shown in Tab. 6 (100 µl, room temperature, 1 h). After the plates had been washed three times with WBB, detection of the bound GM-CSF was effected with the horseradish peroxidase-labeled monoclonal anti-GM-CSF antibody 932/698 (Behringwerke, Marburg, FRG) in the given dilutions in PBS containing 1% BSA (100 µl, room temperature, 30 min.), and subsequent color development in 100 µl of TMB substrate solution (Behringwerke Marburg, FRG). Tab. 6 shows that in this test set-up, and depending on the concentration of antibody-conjugate used, GM-CSF can be detected from a concentration of about 10 pg/ml.

Determination of the Presence and Concentration of Human Interleukin-4

TABLE 1A

| Concentration of human IL-4 (pg/ml) | 5 µg/ml Optical density | hu IL-4R C.V. (%) | 5 µg/ml Optical density | hu IL-4R/Fc C.V. (%) |
|---|---|---|---|---|
| 200 | 3.729 | 5.4 | 4.048 | 3.6 |
| 100 | 1.532 | 0.4 | 3.631 | 2.3 |
| 50 | 0.530 | 5.4 | 1.694 | 2.6 |
| 25 | 0.241 | 5.0 | 0.817 | 4.1 |
| 12.5 | 0.130 | 7.5 | 0.465 | 2.2 |
| 6.25 | 0.102 | 12.4 | 0.340 | 4.9 |
| 3.125 | 0.095 | 28.0 | 0.306 | 11.2 |

TABLE 1B

Controls: The values given are the maximum sample concentrations employed and the concentrations determined from the extinction using Table 1A

| hu IL-1 | α | 719-27 | 7.5 ng/ml | <31 pg/ml |
|---|---|---|---|---|
| hu IL-1 | β | 693-28 | 16.6 ng/ml | <31 pg/ml |
| hu-TNF | α | IMMUNEX 2561-100 SKG 6-25-91 | 50 ng/ml | <31 pg/ml |
| hu-TNF | α | GENZYME B1089 | 50 ng/ml | <31 pg/ml |
| hu IL-2 | | ROUSSEL UCLAF 49637, Lot 22660-162 C | 5000 IU/ml | <31 pg/ml |
| hu IL-6 | | Culture supernatant 980-5-2 | 5000 IU/ml | <31 pg/ml |
| hu IL-7 | | IMMUNEX | 50 ng/ml | <31 pg/ml |
| mu IL-4 | | IMMUNEX | 50 ng/ml | <31 pg/ml |

Determination of the Presence and Concentration of Murine Interleukin-4

TABLE 2A

| Concentration of murine IL-4 (pg/ml) | Proteins used for coating 5 µg/ml mu IL-4R/Fc Optical density | C.V. (%) |
|---|---|---|
| 2000 | 2.533 | 4.24 |
| 1000 | 1.61 | 3.95 |
| 500 | 0.849 | 5.42 |
| 250 | 0.487 | 16.84 |
| 125 | 0.292 | 2.66 |
| 62.5 | 0.191 | 11.85 |
| 31.25 | 0.156 | — |
| 0 | 0.115 | 10.5 |

TABLE 2B

Controls: The values given are the maximum sample concentrations employed and the concentrations determined from the extinction using Table 2A

| mu IL-1 | α | GENZYME B0557 | 100 IU/ml | <31 pg/ml |
|---|---|---|---|---|
| mu IL-1 | β | GENZYME 1921-01 | 10 ng/ml | <31 pg/ml |
| mu-TNF | α | GENZYME B0114 | 100 ng/ml | <31 pg/ml |
| hu IL-4 | | IMMUNEX | 50 ng/ml | <31 pg/ml |

TABLE 3

Sandwich immuno-erythropoietin receptor-assay

Solid-phase bound anti-EPO antibodies having different idiotypes. All the antibodies recognize epitopes which are different from the receptor binding site. The bound erythropoietin was detected using an EPO-receptor-Fc fusion protein coupled to peroxidase.

TABLE 3A

Monoclonal antibody 89-113-069 (Optical density at 492 nm)

| [EPO] in pg/ml | Average value | Standard deviation |
|---|---|---|
| 1000 | 4.029 | 0.053 |
| 500 | 3.466 | 0.034 |
| 250 | 2.528 | 0.057 |
| 125 | 1.548 | 0.029 |
| 63 | 0.872 | 0.025 |
| 31 | 0.507 | 0.012 |
| 16 | 0.268 | 0.016 |
| 8 | 0.130 | 0.006 |
| 4 | 0.066 | 0.004 |
| 2 | 0.045 | 0.003 |
| 1 | 0.034 | 0.003 |
| 0 | 0.021 | 0.003 |
| blank | 0.015 | 0.002 |

TABLE 3B

Monoclonal antibody 89-113-107 (Optical density at 492 nm)

| [EPO] in pg/ml | Average value | Standard deviation |
|---|---|---|
| 1000 | 1.831 | 0.024 |
| 500 | 1.263 | 0.027 |
| 250 | 0.626 | 0.017 |
| 125 | 0.252 | 0.009 |
| 63 | 0.113 | 0.010 |
| 31 | 0.063 | 0.007 |
| 16 | 0.044 | 0.002 |
| 8 | 0.033 | 0.002 |
| 4 | 0.026 | 0.001 |
| 2 | 0.022 | 0.002 |
| 1 | 0.021 | 0.001 |
| 0 | 0.019 | 0.001 |
| blank | 0.016 | 0.001 |

TABLE 3C

Polyclonal rabbit anti-EPO antibody
(Optical density at 492 nm)

| [EPO] in pg/ml | Average value | Standard deviation |
|---|---|---|
| 1000 | 3.053 | 0.033 |
| 500 | 2.248 | 0.022 |
| 250 | 1.153 | 0.031 |
| 125 | 0.585 | 0.019 |
| 63 | 0.296 | 0.020 |
| 31 | 0.157 | 0.007 |
| 16 | 0.094 | 0.005 |
| 8 | 0.065 | 0.004 |
| 4 | 0.046 | 0.003 |
| 2 | 0.034 | 0.003 |
| 1 | 0.026 | 0.001 |
| 0 | 0.025 | 0.002 |
| blank | 0.014 | 0.002 |

TABLE 4

Sandwich immuno-erythropoietin receptor-binding assay

Solid-phase bound anti-human IgG monoclonal antibody (5 μg/ml)
Erythropoietin receptor-Fc-fusion protein (100 ng/ml - 30 min/RT)
The bound erythropoietin was detected using anti-EPO antibodies coupled to horseradish peroxidase.

TABLE 4A

Monoclonal antibody 89-146-050-peroxidase conjugate
(Optical density at 492 nm)

| [EPO] in pg/ml | Average value | Standard deviation |
|---|---|---|
| 1000.0 | 4.206 | 0.079 |
| 500.0 | 2.509 | 0.067 |
| 250.0 | 1.538 | 0.064 |
| 125.0 | 0.822 | 0.010 |
| 62.5 | 0.424 | 0.003 |
| 31.2 | 0.286 | 0.015 |
| 15.6 | 0.145 | 0.007 |
| 7.8 | 0.119 | 0.006 |
| 3.9 | 0.077 | 0.005 |
| 2.0 | 0.064 | 0.005 |
| 1.0 | 0.057 | 0.005 |
| 0.5 | 0.049 | 0.005 |
| 0.2 | 0.042 | 0.002 |
| 0.0 | 0.041 | 0.002 |
| blank | 0.037 | 0.001 |

TABLE 4B

Monoclonal antibody 89-113-069-peroxidase conjugate
(Optical density at 492 nm)

| [EPO] in pg/ml | Average value | Standard deviation |
|---|---|---|
| 1000.0 | 3.953 | 0.061 |
| 500.0 | 3.335 | 0.100 |
| 250.0 | 2.417 | 0.065 |
| 125.0 | 1.479 | 0.045 |
| 62.5 | 0.845 | 0.031 |
| 31.2 | 0.485 | 0.022 |
| 15.6 | 0.262 | 0.026 |

TABLE 4B-continued

Monoclonal antibody 89-113-069-peroxidase conjugate
(Optical density at 492 nm)

| [EPO] in pg/ml | Average value | Standard deviation |
|---|---|---|
| 7.8 | 0.125 | 0.010 |
| 3.9 | 0.064 | 0.005 |
| 2.0 | 0.043 | 0.001 |
| 1.0 | 0.039 | 0.000 |
| 0.5 | 0.040 | 0.004 |
| 0.2 | 0.040 | 0.002 |
| 0.0 | 0.038 | 0.002 |
| blank | 0.038 | 0.002 |

TABLE 4C

Sandwich immuno-erythropoietin receptor-binding assay
Solid-phase bound anti-human IgG monoclonal antibody (5 μg/ml)
Erythropoietin receptor-Fc-fusion protein (100 ng/ml - 30 min/RT)
The bound erythropoietin was detected using anti-EPO antibodies coupled to horseradish peroxidase.

Monoclonal antibody 89-113-107-peroxidase conjugate
(Optical density at 492 nm)

| [EPO] in pg/ml | Average value | Standard deviation |
|---|---|---|
| 1000.0 | 1.986 | 0.012 |
| 500.0 | 1.374 | 0.016 |
| 250.0 | 0.670 | 0.026 |
| 125.0 | 0.277 | 0.015 |
| 62.5 | 0.125 | 0.013 |
| 31.2 | 0.069 | 0.004 |
| 15.6 | 0.049 | 0.003 |
| 7.8 | 0.037 | 0.003 |
| 3.9 | 0.028 | 0.001 |
| 2.0 | 0.024 | 0.002 |
| 1.0 | 0.022 | 0.001 |
| 0.5 | 0.023 | 0.001 |
| 0.2 | 0.020 | 0.001 |
| 0.0 | 0.022 | 0.003 |
| blank | 0.021 | 0.001 |

TABLE 4D

Polyclonal rabbit antibody-peroxidase conjugate 1095
(Optical density at 492 nm)

| [EPO] in pg/ml | Average value | Standard deviation |
|---|---|---|
| 1000.0 | 3.303 | 0.027 |
| 500.0 | 2.446 | 0.127 |
| 250.0 | 1.264 | 0.024 |
| 125.0 | 0.662 | 0.022 |
| 62.5 | 0.354 | 0.016 |
| 31.2 | 0.213 | 0.010 |
| 15.6 | 0.148 | 0.010 |
| 7.8 | 0.113 | 0.903 |
| 3.9 | 0.090 | 0.007 |
| 2.0 | 0.082 | 0.009 |
| 1.0 | 0.072 | 0.003 |
| 0.5 | 0.067 | 0.001 |
| 0.2 | 0.065 | 0.002 |
| 0.0 | 0.065 | 0.004 |
| blank | 0.067 | 0.004 |

TABLE 5

| Solid phase: | Anti-human IgG antibody |
|---|---|
| 1st Step: | Assimilation of the EPO-receptor-Fc fusion protein |
| 2nd Step: | Addition of the samples or of the EPO-Fc fusion protein. |
| 3rd Step: | Addition of a peroxidase conjugate of a monoclonal antibody (89-146-057) which can neutralize the biological effect of EPO. |

| | EPO-Fc | | Glutaraldehyde-EPO dimer/oligomer | |
|---|---|---|---|---|
| [EPO] ng/ml | average | standard deviation | average | standard deviation |
| 1000 | 4.138 | 0.145 | 0.029 | 0.001 |
| 333.3 | 1.731 | 0.064 | 0.028 | 0.002 |
| 111.1 | 0.625 | 0.024 | 0.027 | 0.002 |
| 37.0 | 0.247 | 0.010 | 0.023 | 0.002 |
| 12.3 | 0.092 | 0.004 | 0.024 | 0.001 |
| 4.1 | 0.048 | 0.003 | 0.022 | 0.002 |
| 1.4 | 0.035 | 0.003 | 0.025 | 0.002 |
| 0.5 | 0.028 | 0.003 | 0.024 | 0.003 |
| 0.0 | 0.024 | 0.002 | 0.023 | 0.002 |

TABLE 6

Detection of GM-CSF using a GM-CSF-receptor/Fc fusion protein

| [GM-CSF] | 932/698-POD (µg/ml) | | | | | | | |
|---|---|---|---|---|---|---|---|---|
| in pg/ml | 700 | 350 | 175 | 88 | 44 | 22 | 11 | 0 |
| 1000 | 0.865 | 0.438 | 0.255 | 0.154 | 0.150 | 0.141 | 0.078 | 0.084 |
| 500 | 0.891 | 0.416 | 0.269 | 0.123 | 0.072 | 0.056 | 0.048 | 0.032 |
| 250 | 0.674 | 0.325 | 0.175 | 0.097 | 0.068 | 0.046 | 0.035 | 0.028 |
| 125 | 0.473 | 0.214 | 0.126 | 0.067 | 0.040 | 0.028 | 0.023 | 0.016 |
| 63 | 0.264 | 0.124 | 0.072 | 0.043 | 0.031 | 0.020 | 0.017 | 0.013 |
| 31 | 0.163 | 0.069 | 0.044 | 0.026 | 0.020 | 0.013 | 0.013 | 0.010 |
| 16 | 0.088 | 0.044 | 0.028 | 0.017 | 0.014 | 0.014 | 0.012 | 0.011 |
| 8 | 0.051 | 0.024 | 0.018 | 0.013 | 0.009 | 0.008 | 0.010 | 0.009 |
| 4 | 0.028 | 0.014 | 0.011 | 0.009 | 0.007 | 0.006 | 0.007 | 0.008 |
| 2 | 0.019 | 0.011 | 0.009 | 0.008 | 0.006 | 0.006 | 0.007 | 0.008 |
| 1 | 0.013 | 0.010 | 0.008 | 0.006 | 0.005 | 0.005 | 0.007 | 0.007 |
| 0 | 0.007 | 0.006 | 0.007 | 0.006 | 0.006 | 0.005 | 0.006 | 0.007 |

What is claimed is:

1. A method for determining an analyte in a sample of a liquid medium comprising:
   i) bringing the sample into contact with
      (a) a soluble, recombinant receptor, or derivative thereof, for the analyte, and
      (b) a specific antibody directed against the analyte, to form a receptor-analyte-antibody complex;
   ii) detecting said receptor-analyte-antibody complex; and
   iii) determining the amount of analyte from the amount of said receptor-analyte-antibody complex;
wherein the specific antibody directed against the analyte is bound to a solid phase.

2. The method as claimed in claim 1, wherein (ii) comprises detecting said receptor-analyte-antibody complex by means of the soluble, recombinant receptor, or a derivative thereof, for the analyte.

3. The method as claimed in claim 1, wherein the analyte is a derivative of a naturally occurring mediator.

4. The method as claimed in claim 1, wherein the analyte is present in a dimeric or multimeric form.

5. The method as claimed in claim 1, wherein said analyte is a substance that influences the interaction of pathogenic organisms, selected from the group consisting of viruses and bacteria, with their cellular receptors.

6. The method as claimed in claim 1, wherein the analyte is a substance that influences the interaction of cellular adhesion molecules.

7. The method as claimed in claim 1, wherein the receptor is selected from the group consisting of a cytokine receptor, a hormone receptor, a neurotransmitter receptor, and a cellular receptor for a pathogenic organism.

8. The method as claimed in claim 1, wherein the receptor is selected from the group consisting of interleukin-4 receptor, erythropoietin receptor, interleukin-1 receptor, interleukin-7 receptor, GM-CSF receptor, IL-8 receptor, TMF receptor, and derivatives of those receptors.

9. A method for diagnosing diseases with an increased appearance of TH2 T-cells comprising determining interleukin-4 in a sample using the method as claimed in claim 1 to diagnose a disease characterized by an increased appearance of TH2 T-cells.

10. The method of claim 9, wherein said disease is selected from the group consisting of allergic diseases and infections.

11. A method for detecting a protein analyte in a sample of a liquid medium comprising:
    i) bringing the sample into contact with
       (a) a soluble, recombinant receptor, or a derivative thereof, for the protein analyte, and
       (b) a specific antibody directed against the protein analyte, to form a receptor-protein analyte-antibody complex; and
    ii) detecting said receptor-protein analyte-antibody complex;
wherein the specific antibody directed against the protein analyte is bound to a solid phase.

12. The method as claimed in claim 11, wherein
    in (i), the sample is brought into contact with a specific antibody directed against the protein analyte; and
    in (ii), the antibody-bound protein analyte is detected by means of a soluble, recombinant receptor, or a derivative thereof, for the protein analyte.

13. The method as claimed in claim 11, wherein
    in (i), the sample is brought into contact with a soluble, recombinant receptor, or a derivative thereof, for the protein analyte; and
    in (ii), the receptor-bound protein analyte is detected by means of a specific antibody directed against the protein analyte.

14. The method as claimed in claim 11, wherein the protein analyte is a derivative of a naturally occurring mediator.

15. The method as claimed in claim 11, wherein the protein analyte is present in a dimeric or multimeric form.

16. The method as claimed in claim 11, wherein said protein analyte is a substance that influences the interaction of pathogenic organisms, selected from the group consisting of viruses and bacteria, with their cellular receptors.

17. The method as claimed in claim 11, wherein said protein analyte is a substance that influences the interaction of cellular adhesion molecules.

18. The method as claimed in claim 11, wherein the receptor is selected from the group consisting of a cytokine receptor, a hormone receptor, a neurotransmitter receptor, and a cellular receptor for a pathogenic organism.

19. The method as claimed in claim 11, wherein the receptor is selected from the group consisting of interleukin-4 receptor, erythropoietin receptor, interleukin-1 receptor, interleukin-7 receptor, GM-CSF receptor, IL-8 receptor, TMF receptor, and derivatives of those receptors.

20. A method for diagnosing diseases with an increased appearance of TH2 T-cells comprising detecting interleukin-4 in a sample using the method as claimed in claim 11 to diagnose a disease characterized by an increased appearance of TH2 T-cells.

21. The method of claim 20 wherein said disease is selected from the group consisting of allergic diseases and infections.

* * * * *